United States Patent [19]

Panchison

[11] Patent Number: 5,690,842
[45] Date of Patent: Nov. 25, 1997

[54] ORTHOPAEDIC WIRE WITH AN ENLARGED END AND METHOD OF FORMING THE SAME

[75] Inventor: Clarence M. Panchison, Warsaw, Ind.

[73] Assignee: Zimmer, Inc., Warsaw, Ind.

[21] Appl. No.: 527,149

[22] Filed: Sep. 12, 1995

[51] Int. Cl.⁶ .............. B21J 1/06; B21C 37/04; B21F 21/00; B21F 45/16

[52] U.S. Cl. .............. 219/58; 219/149; 29/33 F; 72/342.1

[58] Field of Search .............. 219/56, 56.1, 56.22, 219/58, 117.1, 149, 150, 152; 29/34 D, 33 F; 72/342.1

[56] References Cited

U.S. PATENT DOCUMENTS

| | | | |
|---|---|---|---|
| 2,570,547 | 10/1951 | Hanna | 219/152 |
| 2,867,715 | 1/1959 | Falge | 219/56.22 |
| 5,054,301 | 10/1991 | Soga et al. | 219/150 R |
| 5,122,146 | 6/1992 | Chapman et al. | 606/102 |
| 5,601,740 | 2/1997 | Eldgridge et al. | 219/56.22 |

OTHER PUBLICATIONS

Zimmer, Inc.—Surgical Technique ZMS Intramedullary Fixation—Literature No. 97-2236-02—1990.
Zimmer, Inc.—Luque™ Spinal Fixation Wire—Cat. p. D 28—Literature No. 97-5000-109—1987.
Zimmer, Inc.—Kuntscher Nail Guide Pin—Cat. p. B 58—Lit No. 97-5000-107—1987.
Zimmer, Inc.—Intramedullary Nail Extraction Surgical Techniques—Literature No. 97-0409-02—1995.

*Primary Examiner*—Geoffrey S. Evans
*Assistant Examiner*—J. Pelham
*Attorney, Agent, or Firm*—Margaret L. Geringer

[57] ABSTRACT

A method of manufacturing a strong orthopaedic wire (30). A block (20) has an opening (26) with an interior diameter which is slightly larger than an outside diameter (28) of the wire (30). The wire (30) is placed within the opening (26) such that an end (36) of the wire (30) extends a predetermined distance (40) above the block (20). The extending end (36) is heated (e.g. by applying an electric current) until the metal from which the wire is made reaches the wire melting point. The molten metal is allowed to fall via gravitational force against the block (20), whereby the extending end (36) forms an enlarged end (42) on the wire (30).

18 Claims, 1 Drawing Sheet

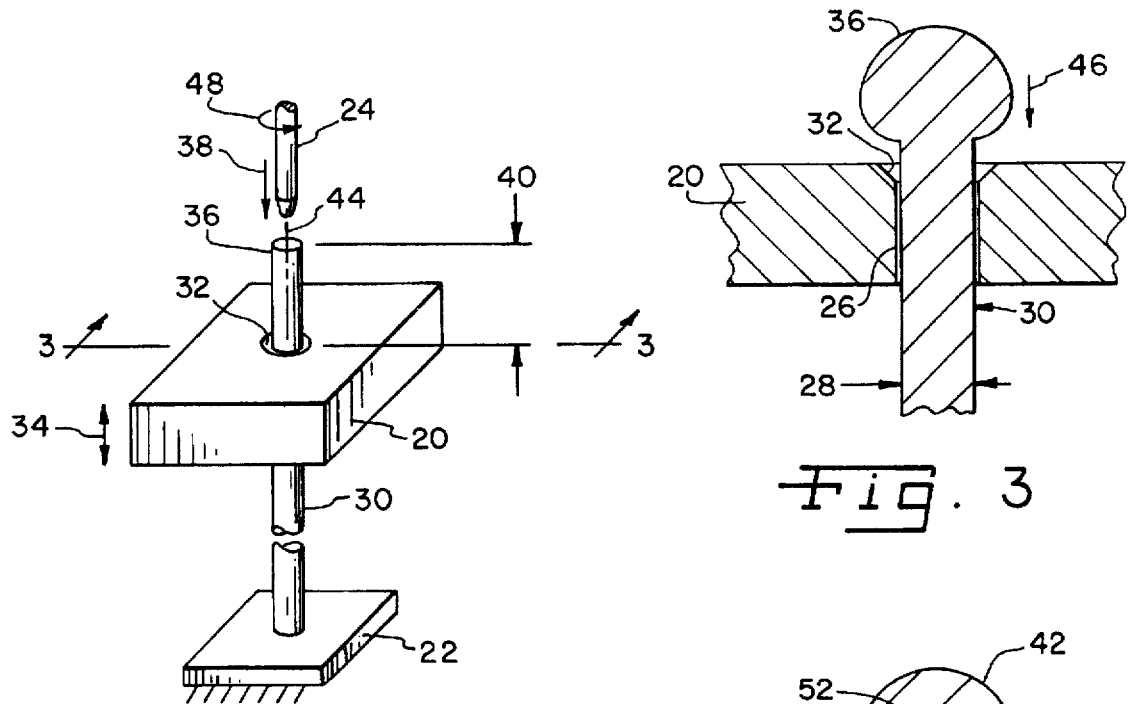

ORTHOPAEDIC WIRE WITH AN ENLARGED END AND METHOD OF FORMING THE SAME

FIELD OF THE INVENTION

The present invention relates to orthopaedic wires, and, more particularly, to orthopaedic wires used during orthopaedic surgery to guide, extract and/or fixate.

BACKGROUND OF THE INVENTION

Orthopaedic wires may be used during orthopaedic surgery for guiding, extracting, and fixating. When used for such purposes, orthopaedic wires typically include an enlarged end commonly known as a ball tip or bullet tip. The enlarged end allows the wire to be guided through an appropriate opening in a bone without significantly damaging the structural integrity of the bone.

For example, it is known to use a wire to guide an intramedullary (IM) nail through a femur or tibia having a fracture. The wire is inserted through the IM canal. The IM nail has an axial opening and is slid over the wire. The wire thereby guides the IM nail through the IM canal and past the fracture site.

It is also known to insert a wire through a broken piece of an IM nail such that the enlarged end extends beyond the IM nail. A second wire (lacking an enlarged end) is then also inserted through the end of the IM nail. The enlarged end is then pulled back against the end of the IM nail and wedges against the second wire, thereby allowing the nail to be pulled from the IM canal. An example of such a process is described in a brochure of Zimmer, Inc. entitled "Intramedullary Nail Extraction Surgical Techniques" in the section for broken cannulated nail extraction (Lit. No. 97-0409-02).

Further, it is known to use a wire to fixate a spine. An example of one such wire marketed by Zimmer, Inc. is known by the trademarked name "Luque Spinal Fixation Wire".

Orthopaedic wires as described above are generally made by two different methods. For smaller diameter wires, the wire is clamped along the longitudinal length thereof and an electrode is placed at a set distance from the end. Electrical power of a known magnitude is applied for a predetermined period of time. The power level is sufficient to raise the temperature of the wire to the melting point of the material, whereby the molten metal essentially "free falls" via gravitational force for the predetermined period of time which the power is applied. This causes a ball tip to be formed at the end of the wire. This is a process by which the "Luque Spinal Fixation Wire" referred to above can be formed.

Although suitable for certain applications, a limitation with such a method is that since the molten metal free falls via gravitational force upon reaching the melting temperature, the ball tip may be disposed other than coaxially with the longitudinal axis of the wire. Another limitation is that depending upon the placement of the electrode, the ball tip may be other than spherically shaped. Additionally, this method cannot be used on orthopaedic wires having a relatively large diameter. That is, if this process is applied to a larger diameter wire, the mass of the molten metal forming the ball tip overcomes the surface tension between the wire and ball tip and the molten metal may fall from the wire. This obviously is not desirable. Further, another limitation is that the time period during which electrical power is applied to the wire and the molten metal free falls is dependent upon the current being passed through the wire. The current must therefore be maintained within relatively small tolerances.

A second method of forming a larger diameter orthopaedic wire having an enlarged end is to weld a machined bullet or ball tip to a wire, such as by upset welding. In general, with upset welding, the machined tip and wire are each clamped and forced together in an axial direction. An electrical current is passed through the machined tip and wire which causes fusion therebetween. The wire is then machined at the point of joining with the machined tip to remove physical irregularities, etc.

A limitation with this method is that it is relatively expensive. The tip must first be machined before joining with the wire. Further machining subsequent to the joining operation is also necessary. This inherently increases the manufacturing cost of wires made by this method. Further, this process cannot be easily used on wires of relatively smaller diameter. When smaller diameter wires are clamped and forced together in an axial direction, the joined ends of the machined tip and wire deflect in a generally radial direction. This offset orientation of the wires relative to each other cannot be easily corrected by machining after the joining process.

Yet another limitation with this method is that voids may exist at the juncture between the machined tip and the wire. That is, depending upon the molecular composition of material at any one point, air gaps between the machined tip and wire at various points, etc., the current passing through the machined tip and wire may not be uniform across the cross-sectional area of the wire. This may result in voids, imperfections, etc., at the juncture between the machined tip and the wire.

What is needed in the art is a method of manufacturing an orthopaedic wire which may be used with either smaller diameter wires or larger diameter wires, which is relatively cost effective, and which does not require joining of the enlarged or ball tip to the wire.

SUMMARY OF THE INVENTION

The present invention provides a method of making an orthopaedic wire, wherein the end of the wire is heated to its melting point and allowed to fall via gravitational force against a block.

The invention comprises, in one form thereof, a method of manufacturing an orthopaedic wire. A block has an opening with an interior diameter which is slightly larger than an outside diameter of the wire. The wire is placed within the opening such that an end of the wire extends a predetermined distance above the block. The extending end is heated until the metal from which the wire is made reaches the wire melting point. The molten metal is allowed to fall via gravitational force against the block, whereby the extending end forms an enlarged end on the wire.

An advantage of the present invention is that no joint exists between the ball tip and the wire, thereby resulting in a stronger wire.

A further advantage is that the ball tip centers itself relative to the longitudinal axis of the wire when using the method of the present invention.

Another advantage is that less scrap occurs using the method of the present invention, thereby reducing manufacturing cost.

A still further advantage is that the electrical current applied to the wire need not be maintained within relatively small tolerances, and in fact the current can be varied manually or automatically.

Yet another advantage is that the electrical current can be applied to the wire for varying periods of time.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a side view of a conventional orthopaedic wire;

FIG. 2 is a schematical, perspective view of an embodiment of structure used to carry out the method of the present invention;

FIG. 3 is a side sectional view taken through line 3—3 in FIG. 2, illustrating formation of an enlarged end on a wire; and FIG. 4 is a side sectional view similar to the view shown in FIG. 3, illustrating a completed enlarged end on a wire.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings and particularly to FIG. 1, a conventional orthopaedic wire 10 is shown. Wire 10 includes a machined tip 12 and a shaft 14 which are connected together at juncture 16, such as by upset welding. Using the upset welding method, machine tip 12 and shaft 14 are forced in an axial direction toward each other, as indicated by directional arrows 18. An electrical current is then passed through machined tip 12 and shaft 14 causing fusion therebetween at juncture 16.

A limitation with conventional orthopaedic wire 10 is that depending upon the molecular composition of material at any one point across juncture 16, air gaps between machined tip 12 and shaft 14 occur across juncture 16. Additionally, the electrical current passing through wire 10 at juncture 16 may not be uniform across the cross-sectional area of wire 10. This may result in voids, imperfections, etc. at juncture 16. Further, because of the compressive axial forces applied to each of machined tip 12 and shaft 14, wire 10 may include a radial bulge at the periphery of juncture 16 which must be subsequently machined smooth.

Referring to FIG. 2, a schematical illustration of structure used to form an orthopaedic wire 30 of the present invention is shown. Orthopaedic wire 30 is constructed of a material consisting essentially of 316L stainless steel or a cobalt chrome alloy, such as L-605. However, wire 30 may be constructed of other suitable materials. In general, the structure used to form wire 30 includes a block 20, fixed surface 22, and electrode 24.

Block 20 is constructed of a nonferrous material such as brass, bronze or copper. Block 20 includes an opening 26 (FIGS. 3 and 4) with an interior diameter which is slightly larger than an outside diameter 28 of wire 30. Block 20 is positioned such that opening 26 extends in a generally vertical direction. A chamfered shoulder 32 is disposed adjacent to opening 26. Block 20 acts as a heat sink for dissipating heat within wire 30.

Block 20 is moveable in a direction corresponding to the longitudinal direction of wire 30, as indicated by multi-directional arrow 34 (FIG. 2). For example, block 20 can be connected either directly or indirectly to a mechanical adjusting device such as a scissor mechanism, a pneumatic device, a hydraulic device, etc. For purposes of clarity and ease of discussion, the many possible variants of structure used to move block 20 are not shown in the drawings.

Fixed surface 22, in the embodiment shown, is in the form of a metal plate which is essentially immovable.

Electrode 24 is connected to an electrical power source (not shown), and is positioned above and substantially coaxially with an end 36 of wire 30. Electrode 24 is movable in a direction toward end 36, as indicated by directional arrow 38.

In use, wire 30 is placed within opening 26 (FIG. 3) of block 20 such that end 36 extends a predetermined distance above block 20, as indicated by distance 40 (FIG. 1). Distance 40 may be adjusted by moving block 20 parallel to longitudinal axis 44 of wire 30, as indicated by arrow 34. In theory, distance 40 is selected such that the volume of end 36 extending above block 20 is the same as the volume of the finished enlarged end above block 20, such as spherical end 42 shown in FIG. 4. However, distance 40 may be adjusted slightly, based upon empirical data, to obtain a spherical end 42 of a particular diameter.

Electrode 24 is moved into close proximity to end 36 (as indicated by arrow 38) and an electrical current is applied to end 36 of wire 30 extending above block 20. The electrical current is of sufficient magnitude to increase the temperature of end 36 to the melting point of the material making up wire 30. During the application of electrical current to extending end 36 through electrode 24, the electrical current can be manually or automatically varied to control the rate of melting or formation of end 36.

Referring now to FIG. 3, wire 30 is shown in the intermediate stage of forming a spherical end 42 (FIG. 4). As electrical current is applied to extending end 36, end 36 melts and falls via gravitational force in a direction towards and against block 20, as indicated by arrow 46. As end 36 moves towards block 20 and enlarges, electrode 24 is moved in a circular motion (indicated by arrow 48 in FIG. 2) relative to longitudinal axis 44 of wire 30. That is, electrode 24 is moved in a rotational direction about longitudinal axis 44. In other words, electrode 24 orbits about longitudinal axis 44.

Referring now to FIG. 4, wire 30 is shown in a completed state, including shaft 50 and spherical end 42. Enlarged end or spherical end 42 is monolithically formed with shaft 50, and includes a central point 52 disposed substantially coaxially with longitudinal axis 44 of shaft 50. Spherical end 42 falls against chamfered shoulder 32, which aids in forming the desired shape of spherical end 42. Moreover, because block 20 is formed from a nonferrous material as indicated above, fusion between spherical end 42 and block 20 does not pose a problem. When spherical end 42 is disposed in the position against chamfered surface 32 of block 20 as shown in FIG. 4, electrode 24 can be moved about the periphery thereof to change, correct or shape spherical end 42 to a more uniform appearance. Block 20 enables this shaping to be done without the enlarged end 42 continuing to fall down wire 30, thus maintaining the desired size and position of end 42 on wire 30.

As will be appreciated by those skilled in the art, heat which is generated in end 36 of wire 30 is transmitted down wire 30 to block 20. The radial tolerance between wire 30 and opening 26 is about 0.002 inch. At least a portion of wire 30 is thus likely to be in contact with inside diameter 26, which allows heat transfer from wire 30 to block 20. The nonferrous material from which block 20 is constructed therefore provides the dual functionality of acting as a heat sink for dissipating heat generated within wire 30, as well as preventing fusion between spherical end 42 and chamfered shoulder 32. The block 20 further provides a support surface for the enlarged end 42 to fall against. By predetermining the distance 40 for a given diameter wire, the desired size for enlarged end 42 can be controlled.

Orthopaedic wire 30 shown in FIG. 4 has an enlarged end or spherical end 42 with a central point 52 disposed substantially coaxially with a corresponding shaft longitudinal axis 44. Block 20 can be used to make a plurality of wires in successive fashion, whereby a plurality of orthopaedic wires 30 can be provided. For ease of discussion, however, only a single orthopaedic wire 30 is shown in FIG. 4.

Using the method set forth above, the following empirical data corresponding to one embodiment of the invention has been established:

TABLE 1

| WIRE DIAMETER | TUNGSTEN ELECTRODE DIAMETER | AMPS | ARGON | DISTANCE ABOVE BLOCK | SPHERICAL END DIAMETER |
|---|---|---|---|---|---|
| 0.063 | 0.063 | 20 | 30 | 0.200 | 0.110 |
| 0.078 | 0.040 | 25 | 30–35 | 0.155 | 0.118 |
| 0.093 | 0.063 | 30 | 30 | 0.270 | 0.157 |
| 0.093 | 0.063 | 30 | 30–35 | 0.335 | 0.170 |
| 0.095 | 0.063 | 30 | 30–35 | 0.237 | 0.150 |
| 0.118 | 0.063 | 30 | 30–35 | 0.300 | 0.188 |
| 0.125 | 0.063 | 35 | 30–35 | 0.270 | 0.197 |
| 0.125 | 0.094 | 40 | 30–35 | 0.480 | 0.236 |

Dimensions are in inches except for the column labeled ARGON, which is in cubic feet per hour (CFH). Using the above parameters, selecting a distance as indicated results in spherical end 42 having a diameter as indicated within approximately ±0.002 inch.

In the embodiment shown in the drawings, block 20 is movable along the longitudinal length of wire 30, and fixed surface 22 is essentially immovable. However, it is also possible that in another embodiment of the invention (not shown), fixed surface 22 can in fact be movable in a direction corresponding to the longitudinal direction of wire 30, and block 20 can be essentially immovable. Other structures and methods for positioning the extending end 36 of wire 30 relative to the top of block 20 are also contemplated by the present invention.

Further, in the embodiment shown, end 36 of wire 30 is heated to its melting point using electrical current passed through electrode 24. However, it is also to be understood that end 36 of wire 30 can be heated to its melting point using an alternate energy source, such as an oxygen/acetylene torch. In such event, molten metal at end 36 still falls via gravitational force against block 20.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing an orthopaedic wire, comprising the steps of:

providing a block having an opening therethrough, said opening sized to receive the wire therein;

placing the wire within said opening such that an end of the wire extends a predetermined distance above said block;

applying an electrical current to the extending end of the wire, said electrical current being of sufficient magnitude to increase the temperature of the extending end to the melting point of the wire; and allowing the molten metal to fall via gravitational force against the block, whereby said extending end forms an enlarged end on said wire.

2. The method of claim 1, comprising the further step of applying electrical current to said extending end after said molten metal falls against said block, whereby said extending end forms a generally spherical end.

3. The method of claim 1, comprising the further step of positioning said block such that said opening extends in a generally vertical direction, said positioning step occurring prior to said placing step.

4. The method of claim 1, wherein said block includes a chamfered shoulder adjacent said opening, and wherein said allowing step comprises allowing the molten metal to fall via gravitational force against said chamfered shoulder.

5. The method of claim 1, comprising the further step of positioning an electrode adjacent the end of the wire, said positioning step occurring prior to said applying step.

6. The method of claim 5, comprising the further step of moving said electrode in an orbital motion relative to a longitudinal axis of the wire and adjacent said end.

7. The method of claim 5, comprising the further step of moving said electrode towards said extending end.

8. The method of claim 1, wherein said placing step results in a volume of the wire extending above the block which is approximately equal to the volume of the enlarged end which is formed at said extending end of the wire.

9. The method of claim 1, wherein the wire is constructed of a material consisting essentially of 316L stainless steel.

10. The method of claim 1, comprising the further step of varying said current which is applied to the extending end.

11. The method of claim 1, wherein said block acts as a heat sink for dissipating heat in the wire.

12. The method of claim 1, wherein the block is constructed of a nonferrous material.

13. The method of claim 1, wherein the opening is provided with an interior diameter which is slightly larger than an outside diameter of the wire.

14. A method of manufacturing an orthopaedic wire, comprising the steps of:

providing a block having an opening therethrough, said opening sized to receive the wire therein;

placing the wire within said opening such that an end of the wire extends a predetermined distance above said block;

heating the extending end until the metal from which the wire is made reaches an associated melting point; and allowing the molten metal to fall via gravitational force against the block, whereby said extending end forms an enlarged end on said wire.

15. The method of claim 14, wherein said heating step comprises applying an electrical current to the extending end of the wire, said electrical current being of sufficient magnitude to increase said temperature of said extending end to said melting point.

16. The method of claim 15, wherein said applying step comprises positioning an electrode adjacent the end of the wire.

17. The method of claim 14, wherein said block comprises a one-piece block.

18. The method of claim 14, wherein the opening is provided with an interior diameter which is slightly larger than an outside diameter of the wire.

* * * * *